United States Patent
Wyrsta et al.

(10) Patent No.: US 7,611,731 B2
(45) Date of Patent: Nov. 3, 2009

(54) MESOSTRUCTURED SILICA/BLOCK COPOLYMER MONOLITHS AS A CONTROLLED RELEASE DEVICE AND METHODS OF MANUFACTURE

(75) Inventors: Michael D. Wyrsta, Santa Barbara, CA (US); Mark L. F. Phillips, Hayward, CA (US)

(73) Assignee: SBA Materials, Inc., Goleta, CA (US)

( * ) Notice: Subject to any disclaimer, the term of this patent is extended or adjusted under 35 U.S.C. 154(b) by 903 days.

(21) Appl. No.: 11/203,495

(22) Filed: Aug. 12, 2005

(65) Prior Publication Data

US 2006/0034924 A1     Feb. 16, 2006

Related U.S. Application Data

(63) Continuation-in-part of application No. 11/134,572, filed on May 19, 2005.

(60) Provisional application No. 60/601,910, filed on Aug. 16, 2004.

(51) Int. Cl.
*A61K 9/14*     (2006.01)
*A61K 9/16*     (2006.01)
*A61B 5/055*    (2006.01)

(52) U.S. Cl. ............... 424/490; 424/9.32; 424/489
(58) Field of Classification Search ............... None
See application file for complete search history.

(56) References Cited

U.S. PATENT DOCUMENTS

2009/0011002 A1*  1/2009  Zabicky et al. ............. 424/450

* cited by examiner

*Primary Examiner*—S. Tran

(57) ABSTRACT

The invention comprises the design, synthesis, and characterization of mesostructured silica/block copolymer composite monoliths as controlled release systems. The controlled release function is based on the formation of mesostructured silica/block copolymer architectures via surfactant-templated sol-gel processing. Multi-layered or gradient monoliths are produced by layer-by-layer sol-gel processing to provide pulsed and programmed release characteristics. A simple, rapid route to prepare combinatorial compositional monolith libraries provides high-throughput synthesis and rapid screening of the release characteristics of the monoliths.

7 Claims, 4 Drawing Sheets

MESOSTRUCTURED SILICA/BLOCK COPOLYMER MONOLITHS AS A CONTROLLED RELEASE DEVICE AND METHODS OF MANUFACTURE

CLAIM OF PRIORITY

Applicant claims priority based on provisional patent application Ser. No. 60/601,910 filed Aug. 16, 2004, the entire contents of which are incorporated herein by reference.

CROSS-REFERENCE TO RELATED APPLICATIONS

This application is a continuation-in-part of application Ser. No. 11/134,572 filed May 19, 2005, currently pending, the entire contents of which are incorporated herein by reference.

TECHNICAL FIELD

The present invention relates to mesoporous polymer/inorganic oxide hybrid material host compositions for controlled release of molecular species. More particularly the invention relates to films, fibers, monoliths, powders or coatings comprising mesoporous polymer/inorganic oxide hybrid materials having release agents incorporated therein for use as controlled release media.

BACKGROUND OF THE INVENTION

When a chemical substance is incorporated into a solid material, a controlled release system is important in order to facilitate release of the chemical substance at a designated rate. Controlled release systems are particularly needed in the medical field where controlled drug delivery is required, and in various industrial applications where a controlled chemical release is required such as agricultural chemical applications, cosmetics, and catalysis.

Heretofore, various techniques and materials have been proposed for controlled release systems, but most are directed to mixing a chemical substance into a polymer gel or forming a complex consisting of a chemical substance and a polymeric material such as organic poly(lactic acid) or wholly inorganic material such as porous silica. Although silica gels are versatile and can incorporate various types of chemical substances therein, the release of substances from the silica matrix comprises a diffusion release mechanism and therefore rapidly decreases.

In recent years liquid solutions or coating films, which comprise surfactant molecules as the main component, have begun to emerge as promising controlled release materials. As a result of trends toward more complex controlled release materials with the proper release profile and safety, polymer surfactant molecules have been rigorously researched and have found use as controlled release agents.

However, many of the polymer coatings and formulations used in controlled release applications lack the ability to tune the release profile of the encapsulated molecular species. Further, the polymer erodes and the chemical substance is released into the environment. Also many controlled release formulations are liquid and therefore lose their ability to control the release of their contents upon dilution.

What is needed is a release device with release characteristics which can be easily tuned over a wide range.

SUMMARY OF THE INVENTION

The present invention comprises a design, synthesis, and characterization of mesostructured inorganic metal oxide composites in the form of films, powders, monoliths, and/or fibers as controlled release systems capable of providing a material having low toxicity and tunable profiles of release of contents which overcomes the foregoing and other difficulties which have long since characterized the prior art. In accordance with the broader aspects of the invention, the present invention relates to the formation of mesostructured inorganic metal oxides for obtaining a controlled release rate using a silica matrix and a polymer that can be eroded or eluted from the matrix. By controlling the architecture formation and the pore size of the inorganic metal oxide composite, the release characteristics can be tuned over a wide range.

In accordance with more specific aspects of the invention, surfactant-directed silicate polymerization is a suitable method to form inorganic metal oxide architectures. The obtained silica/polymer composites are called mesostructured silica, which were first reported in 1992 and have attracted a great deal of interest in synthesis study and applications exploration. The sol-gel based polymer self-assembly and silicate polymerization offers control over the silica/polymer architectures, which significantly enhance the control of the doped compound therein, for example, a dye. Therefore, mesostructured silica has been recognized as potential advanced optical materials, particularly as host media for molecules and complexes exhibiting optical functionalities.

The use of nonionic-surfactants as structure-directing agents (SDAs) and acidic conditions for polymerization allow a wide range of compositions, mesoscopic structures and morphologies to tailor mesostructured silica with desired properties. Moreover, the nonionic surfactants used in mesostructured materials synthesis, generally Pluronic block copolymers, have been be used for drug delivery because of the fact that the core-shell architecture of Pluronic micelles are efficient carriers for compounds. The additional silica matrices in the present invention contribute greatly to the enhanced storage property by maintaining the micelles in a dispersed state, as well as by increasing the incorporation ability of various therapeutic reagents, which alone exhibit poor solubility, undesired pharmacokinetics and low stability in a physiological environment. Furthermore, the use of amphiphilic block copolymers as a template for inorganic metal oxides provides a range of topologies including cubic, hexagonal, and lamellar, and a range of pore sizes from approximately 3 mn to approximately 30 nm thereby enabling tunable release characteristics.

Notwithstanding the superior performance offered in some applications by the pore size and intrapore chemistry of the Pluronic-templated mesostructured oxides, it is to be understood that some applications will benefit from the pore size range (ca. 1-5 nm) available with mesoporous oxides templated with monomeric surfactant micelles such as the MCM-41 and MCM-48 phases.

The controlled release from silica monoliths is based on modifying the polymer elution rate and the matrix diffusion rate. The rate of and duration of compound release can be tuned over a wide range by many factors, including matrix composition, physical structure of the system, morphology, the release media and the physicochemical properties of the compound itself. The advantages of the release devices of the present invention also include supporting very long release duration, easily removable, various morphologies (monolith, film) for further fabrication and versatile for the incorporation of molecules with different physicochemical properties. Moreover, in combination with a layer-by-layer sol-gel processing approach, multi-layered or gradient monoliths can be produced, thereby providing applications in pulsed and programmed release. The present invention comprises a general method to fabricate a controlled-release device that is compatible with various active agents to offer modified release dynamics. Further, the present invention comprises a simple, rapid route to produce combinatorial compositional monolith libraries for the high-throughput synthesis and screening of monoliths with the desired release characteristics, which can be extended to the preparation of multi-layered or gradient monoliths.

The resulting mesoporous polymer/inorganic oxide hybrid material host are applicable to applications requiring a controlled release of a molecular entity(s) such as oral delivery of human and non-human therapeutics, coated biomedical devices, the dispersal delivery agent for agriculturally relevant molecules, various personal care and food products, biocidal and/or pest resistant materials, and corrosion inhibiting agents.

BRIEF DESCRIPTION OF THE DRAWINGS

A more complete understanding of the present invention may be had by reference to the following Detailed Description when taken in connection with the accompanying Drawings, wherein.

DETAILED DESCRIPTION

Figure 1:
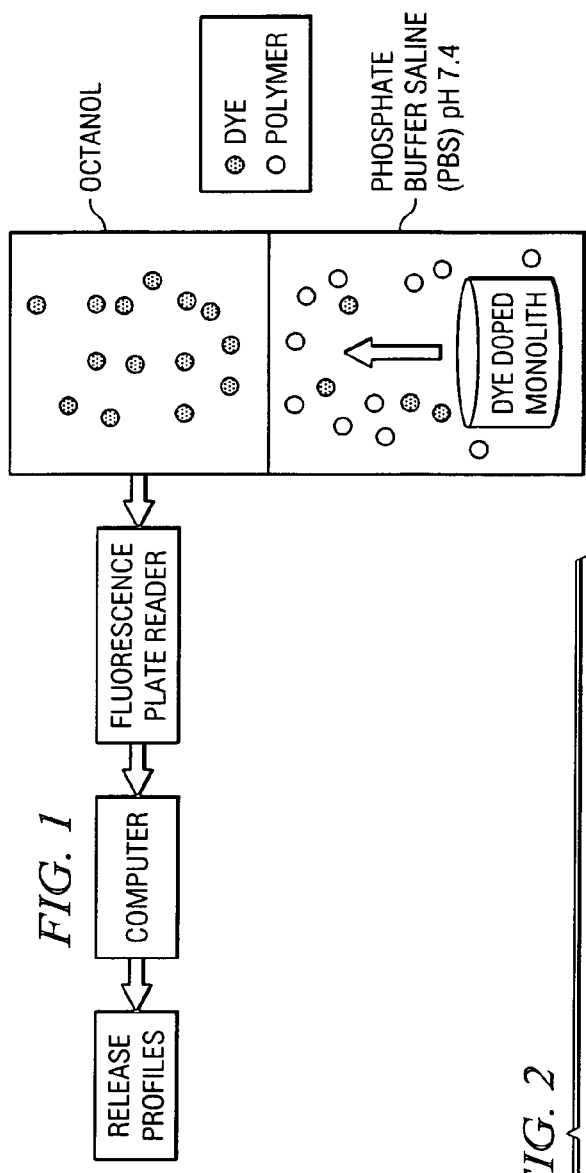
FIG. 1 illustrates one step in the preparation of the mesostructured silica/block copolymer monoliths of the present invention.

General methods of Incorporating Release Agents for Controlled Release into Mesoporous Hosts Methods for including release agents into the mesostructured hosts include the following:

a. The release agent is mixed with the starting materials that form the sol and thereafter becomes contained within the silica/polymer composite. The size of the pores and the molecular weight of the polymer control both the rate at which the agent diffuses through the polymer and the rate at which the polymer erodes. This method (termed "sol incorporation") is equally applicable to thin films, free standing thick films, monoliths, and powders. In some manifestations the release agent may also function as the polymer template, such as polypeptide-templated mesostructures.

b. A solid or liquid release agent is encapsulated by a silica/polymer composite. The agent can be in particle or droplet form, or it can be a solid monolith, or a coating on an inert surface. In the latter case the mesoporous silica is cladded onto the agent, treated to remove the polymer template, and further treated with surface modifiers that alter chemistry to control the release rate and/or the chemical conditions under which the agent is released. This method is termed "encapsulation".

c. A film, monolith, or powdered mesoporous silica is immersed in the release agent or a solution of the agent, which becomes incorporated into the mesostructured inorganic/polymer composite and is available for subsequent release. Alternately the polymer template may have been previously removed from the inorganic framework prior to incorporation. The inorganic framework may be functionalized to yield a surface chemistry that improves release characteristics of a particular agent. This method is termed "impregnation".

d. In some manifestations the release agent may also function as the polymer template. Such template may be selected to break down, releasing desired component(s) after a certain time or under the appropriate chemical conditions. Polypeptide-templated mesostructures fall under this category.

Some applications require two or more release agents to be kept separate from one another prior to receiving an external stimulus such as a change in physical or chemical environment. This is accomplished by sequentially layering the films into a multiplayer structure. This method is particularly useful for use in biocidal films, wherein the chemical activity depends on simultaneous release of peroxide and a peroxide activator. The peroxide and peroxide activator must remain separate when release activity is not required. When release is required, the two release agents thereafter elute and react together upon wetting the film.

Experimental Development of the Present Invention

The chemical reagents used for the synthesis include the following: Pluronic L64 ($EO_{13}PO_{30}EO_{13}$, $M_{av}$=2900, PEO wt %=40%; Aldrich), Pluronic P84 ($EO_{19}PO_{43}EO_{19}$, $M_{av}$=4200, PEO wt %=40%; Aldrich), Pluronic P104 ($EO_{27}PO_{61}EO_{27}$, $M_{av}$=5900, PEO wt %=40%; Aldrich), Pluronic F88 ($EO_{104}PO_{39}EO_{104}$, $M_{av}$=11400, PEO wt %=80%, Aldrich), and tetraethyl-orthosilicate (TEOS, Merck). The fluorescence dyes employed in this study were Rhodamine 6G (Molecular Probe) and LD 490 (Exciton). It is to be understood that these dyes are intended to approximate the release characteristics of small molecules that are relevant to a desired application, and that the scope of this invention is not limited to release of agents that are physically or chemically similar to the above-identified dyes.

Sample Preparation

The following example illustrates the synthesis of a silica/polymer monolith doped with a dye representing a desired release agent, using the sol incorporation technique.

1. Preparation of Dye-Containing Mesostructured Silica/Block Copolymer Composite Monolith Dye-containing mesostructured silica/block copolymer composite monoliths were prepared in standard 96-well plate through an evaporation-induced self-assembly (EISA) sol-gel processing, as follows. A block copolymer was dissolved in a sol of TEOS/water/ethanol that was pre-hydrolyzed at 60° C. for 2 hours, forming a homogeneous solution. A fluorescent dye was then dissolved in the sol, which was then transferred to a standard 96-well plate for gelation of monoliths. In each well, 200 µL sol and 5 µL dye (1 µmol) were pipetted. These monoliths were gelled and dried at ambient environment for 3 days and at 60° C, in an oven for 1 day.

2. Library Design

Combinatorial compositional monolith libraries were prepared for high-throughput synthesis and screening of the monolith with desired release characteristics. L64, P84, P104 and F88 were used in this work. For the library of each block polymer, the initial polymer mass content was 0%, 1%, 3%, 5%, 7%, 10%, 15% and 20%, and the molar composition was TEOS:HCl (pH=2):ethanol=1:(4, 8, 12):(4, 12, 20).

3. Release Set-up

The set-up of the release profiles is illustrated in FIG. 1. The fluorescent dye doped in the monoliths was released in the wells of a 96-well deep plate. The release medium was an aqueous buffer having a pH of 7.4 at a temperature of 25° C. and octanol was introduced to extract released dye for concentration analysis. For each well, a piece of monolith was immersed in 400 µL of aqueous buffer (pH=7.4), followed by adding 600 µL of octanol.

Analytical Method of the Present Invention

1. Investigation of Release Profiles

In this study, fluorescent dyes Rhodamine 6G and LD 490 were employed as model compounds for release. The amount of released dye was determined by monitoring changes of fluorescence intensity, which was measured using a fluorescence plate reader (HTSoft 7000; PerkinElmer) (485 nm excitation, 595 nm emission for Rhodamine 6G and 430 nm excitation, 535 nm emission for LD 490). For a typical procedure, 5 µl solution of the octanol layer was transferred to the well of a standard 96-well plate, followed by adding 195 µl 5:1 volume ratio of ethanol/water for dilution. A series of standard solutions that were comprised of known concentrations of fluorescence dye were pipetted to the remaining wells of the plate as reference. The samples were rotated for 1 minute at 25° C. Precise readings of the well's fluorescence and then reference curves based on the fluorescence response of standard solutions were prepared to quantitatively calculate the released amount of dye from these monoliths.

More generally, it is possible to tailor the rate of release by optimizing the silica host/polymer template/surface modifier systems to provide a desired release rate for the specified release agents when a chemical "signal" is detected. Release can also be staged or programmed to have a desired temporal profile, e.g., "first order" (release rate slowly decays to zero), "zero order" (release rate is constant until agent is exhausted), or a "spiked release" in which a large quantity of agent is released after a desired delay.

When applied in conjunction multilayer films/multiple agents, different agents are released in sequence, or, a combination of agents is held separately and released simultaneously under the desired chemical stimulus.

2. Determination of Model Compound Content

To determine model compound content and remaining amount dyes after release, the dye-doped monolith was dissolved in 10 ml 2M NaOH with 1:1 ethanol/water (v/v) by overnight rotation; then a 400 µl volume of the above solution was pipetted to a well of a deep plate and followed by 600 µl octanol to extract the dye. The dye content is then determined by the method described above.

Characterization Methods of the Present Invention

Release profiles were investigated by a Perkin Elmer HT Soft 7000 Plus Bio Assay Reader, which is designed for luminescence and adsorption readings of various microplates. For fluorescence analysis, the excitation wavelength used was 485 nm and analysis wavelength was 595 nm for Rhodamine 6G. For LD 490, excitation and analysis wavelengths were 430 nm and 535 nm. X-ray diffraction (XRD) patterns were obtained on a Scintag PAD X diffractometer employing Cu Kα radiation. Transmission electron microscopy (TEM) was performed a JEOL 2000 FX after drying of samples at 373 K for 4 hours.

Results and Discussion

Figure 2:
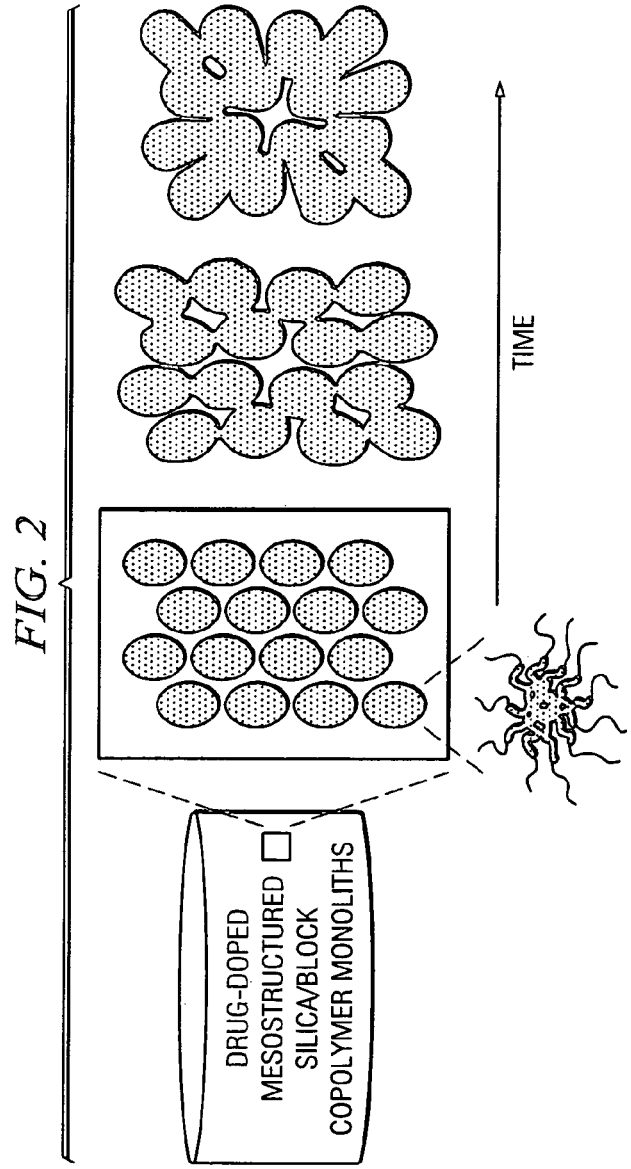
FIG. 2 illustrates the controlled release of the doped mesostructured silica/block copolymer monoliths of the present invention.

The concept of controlled release of the doped mesostructured silica/block copolymer monolith is shown in FIG. 2. The incorporated dyes are located in the polymer phase of the silica polymer architecture, which is powerful in incorporating and stabilizing not only hydrophilic but also hydrophobic molecules and DNAs. In the release process, water molecules penetrate the silica framework and erode the polymer to release the dyes. Dye molecules are then diffused with the eroded polymer from the silica framework. The release rate is determined by the polymer eroding rate, which can be controlled through known factors. A dye containing mesostructured silica/block copolymer monoliths demonstrated an evident color difference of the dye content. A gradient monolith prepared by layer-by-layer method demonstrated an evident color change, demonstrating the concentration of dye is gradually changed along the axis or radius because of the diffusion between the interfaces.

Figure 3A:
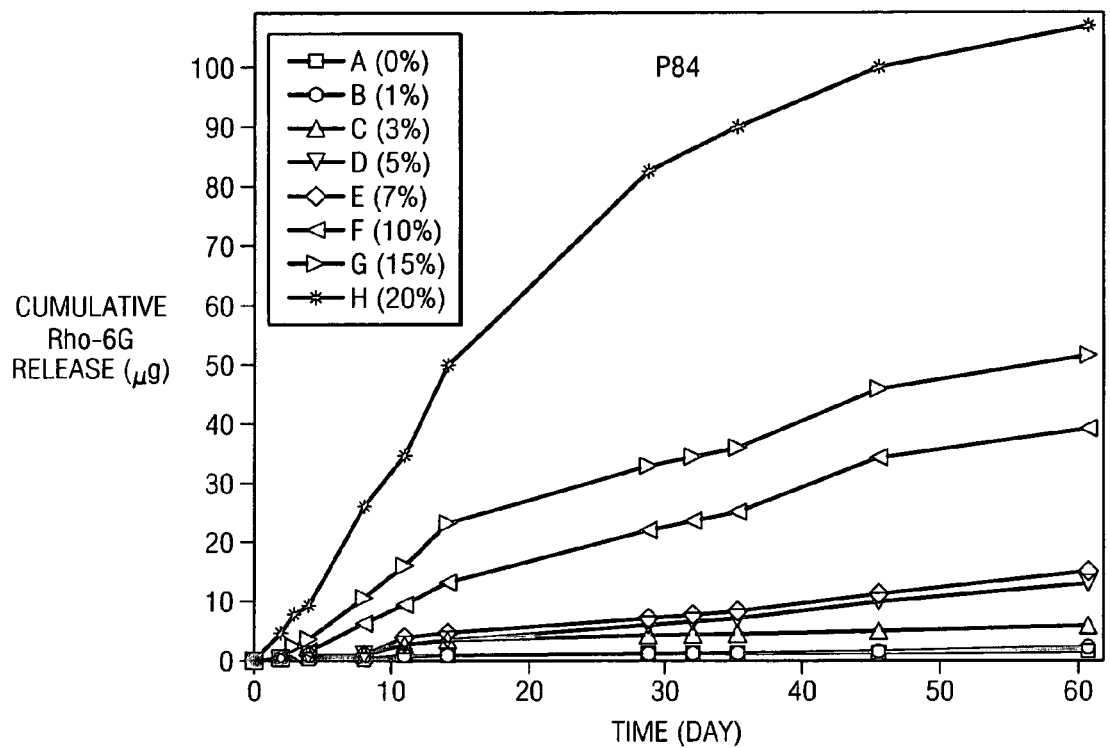
FIG. 3A is a graphical representation of the differential release profiles of Rhodamine 6G from the mesostructured silica/block copolymer monoliths of the present invention contained therein.
Figure 3B:
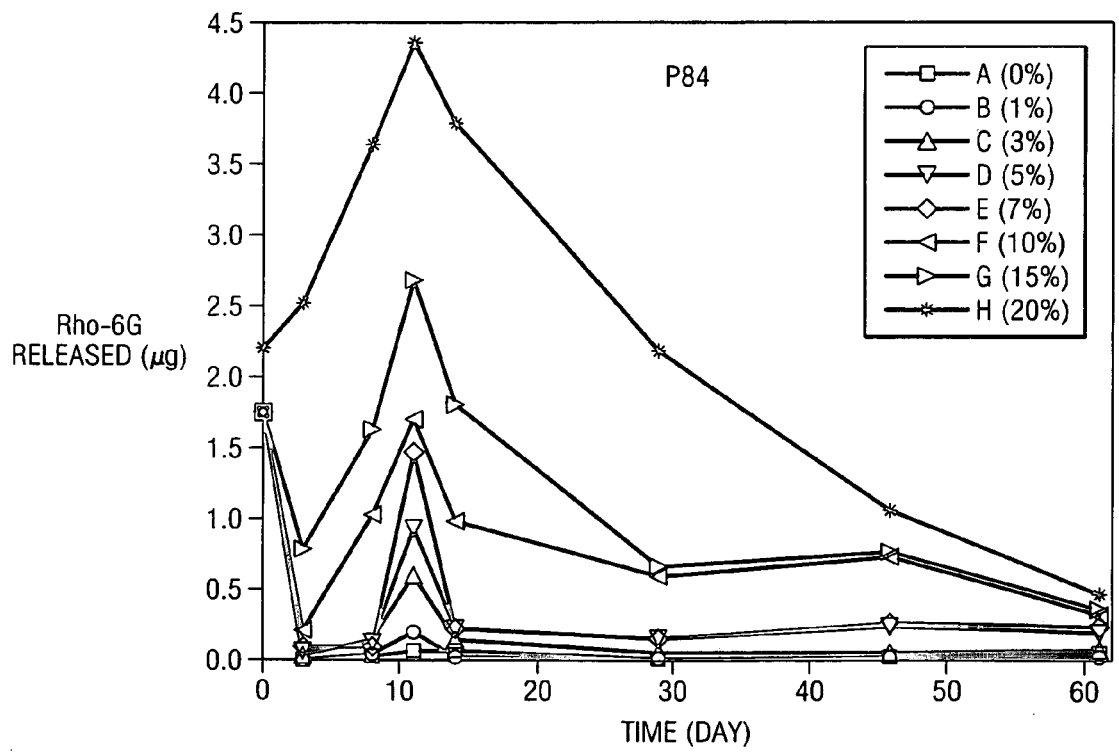
FIG. 3B is a graphical representation similar to FIG. 3A showing the cumulative release profiles of Rhodamine 6G from the mesostructured silica/block copolymer monoliths of the present invention contained therein.

FIGS. 3A and 3B show the typical cumulative and differential release profiles of Rhodamine 6G-containing mesostructured silica/block copolymer monoliths with different polymer concentrations (0%-20%) for the first 2 months. These monoliths were doped with same amount of Rhodamine 6G (480 µg per monolith, which was confirmed by the dye-content-determination experiment) and prepared by Pluronic P84 and a sol of TEOS:HCl (pH=2):ethanol=1: 4:4 (molar ratio) through sol-gel processing. The initial P84 mass concentrations of the monoliths are 0%, 1%, 3%, 5%, 7%, 10%, 15% and 20%. The cumulative release profiles shown in FIG. 3A demonstrate the feasibility of modifying the release rate by tuning the polymer concentrations in the monolith. The release rate increased with respect to the increasing polymer concentrations. After 2 months, released Rhodamine 6G varied from 1.7 µg to 107 µg.

Referring to FIG. 3B, more release characteristics are shown in the differential release pattern, facilitating clarification of the release dynamics. Three-phase mode release profiles were evident with an initial burst reaching 0.07 µg in the first hour due to the surface localized dye molecules, followed by a decline through day 3. The release rate increased again at around day 11 and then decreased slowly or reached a plateau through day 62. The release pattern of Rhodamine 6G in mesostructured monolith does not have a high burst release nor the occurrence of an extended period of little or no release. This release pattern indicated a simultaneous occurrence of matrix diffusion and polymer elution, as compared with the purely diffusion-controlled release kinetics calculated from the classical Higuchi equation. The release rate will clearly increase with time by the increasing dye permeability of the system with progressive polymer elution. This is the second phase of the release pattern.

Similar results occur during polymer bulking eroding process, in which water uptake by the system is much faster than polymer eroding. However, after a certain time period this effect is overcompensated by a diffusion-controlled release, due to increasing diffusion pathlengths of polymers and dyes. Thus, the release rate will slowly decrease or reaches a plateau, which is recognized as the third phase of the release pattern.

Figure 4:
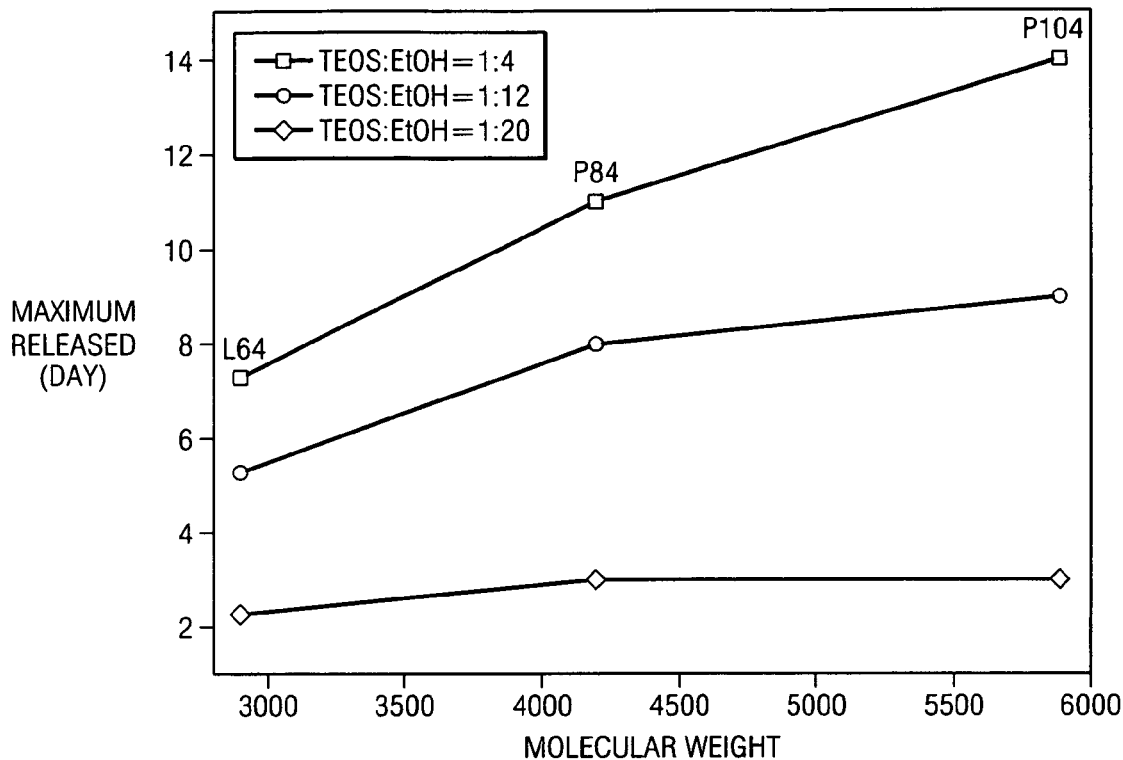
FIG. 4 is a graphical representation of peaks of the differential release patterns as they relate to the polymers themselves and water-soluble molecules remaining in the monolith.

The peak in the differential release pattern reflects the transition from phase 2 to phase 3, which is influenced by the factors of monolith composition. The position of peaks relates to the polymers themselves and water-soluble molecules remaining in the monolith as shown in FIG. 4. For polymers with same PPO content, the smaller molecular weight, the easier the polymer is eluted. Further, for a monolith with much ethanol remaining, the monolith will hydrate more rapidly than it will be eluted. For example, in FIG. 4, with increasing molecular weight of L64, P84 and P104, the peaks appeared on day 7.3, 11 and 14, respectively. Increasing the mole ratio of ethanol/TEOS, the peak appeared at an earlier day. In the condition of TEOS/ethanol=1:20, the peaks of L64, P84 and P104 appeared at the nearly same day, which can accounted for too much ethanol resulting in very fast hydration and elution. The height of the peak is therefore influenced by the polymer concentration, which corresponds to the dye permeability during polymer elution.

Figure 5A:
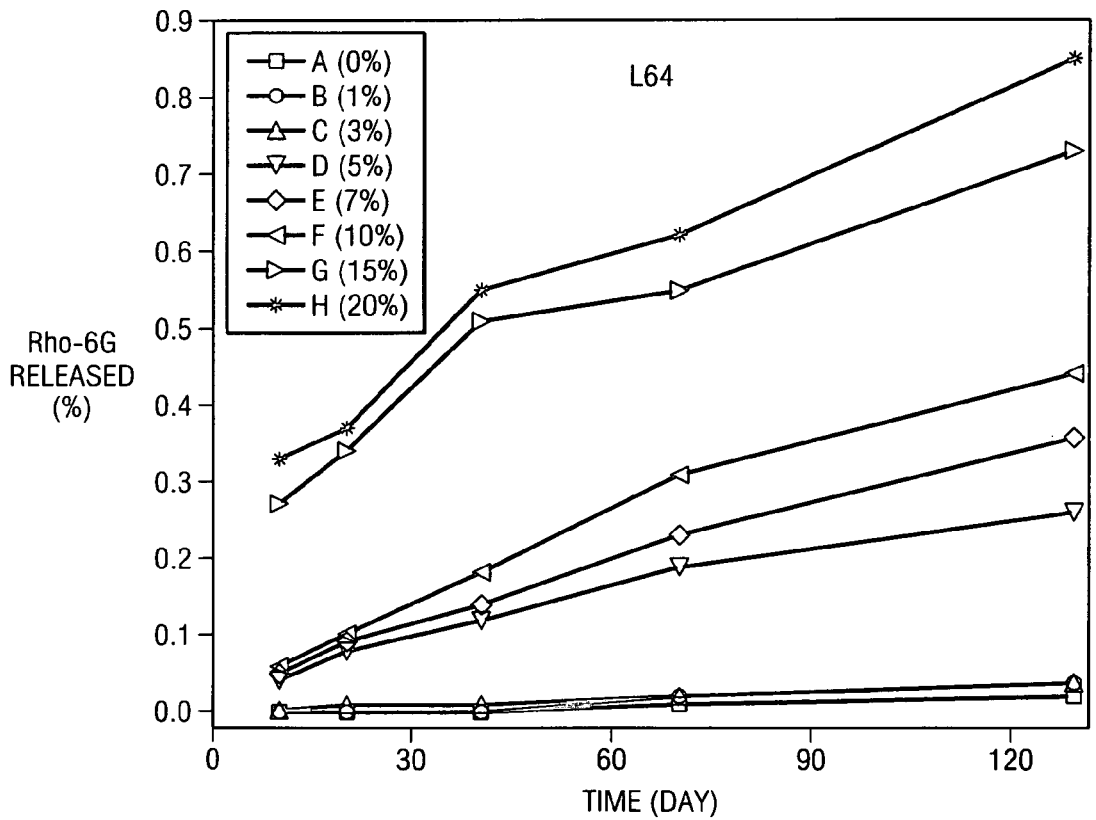
FIG. 5A is a graphical representation of the present release profile of a selected block copolymer.
Figure 5B:
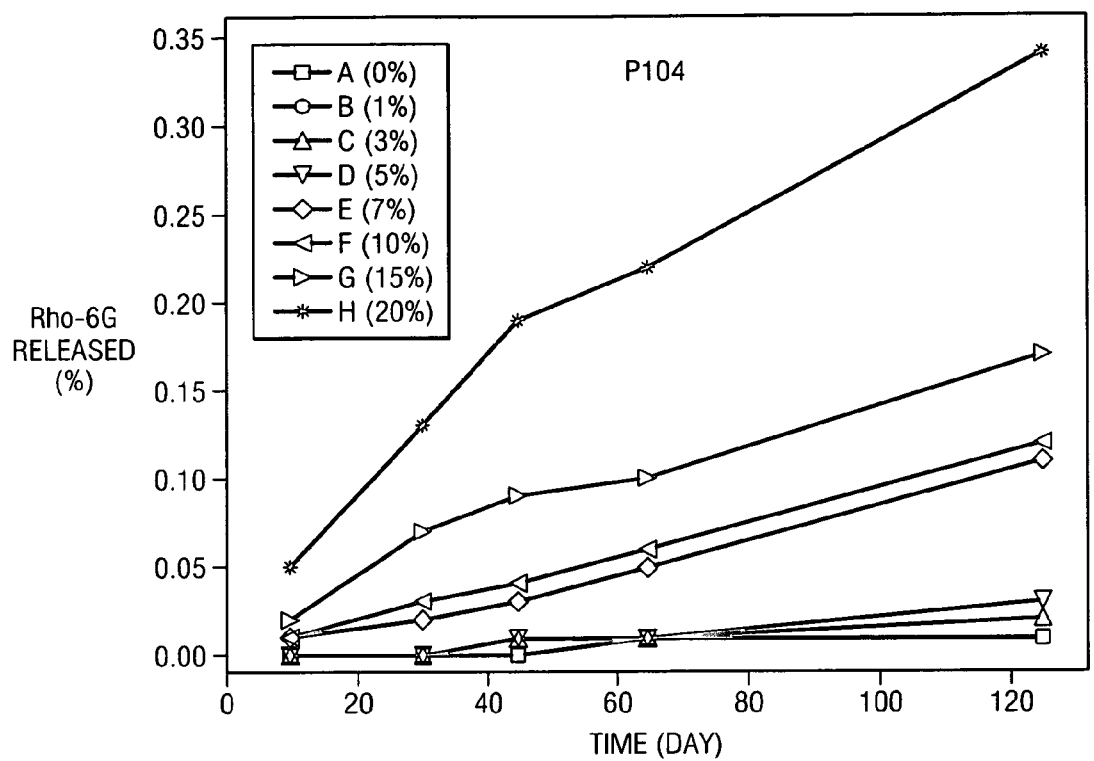
FIG. 5B is a graphical representation similar to FIG. 5A showing the release profile of another block copolymer.
Figure 5C:
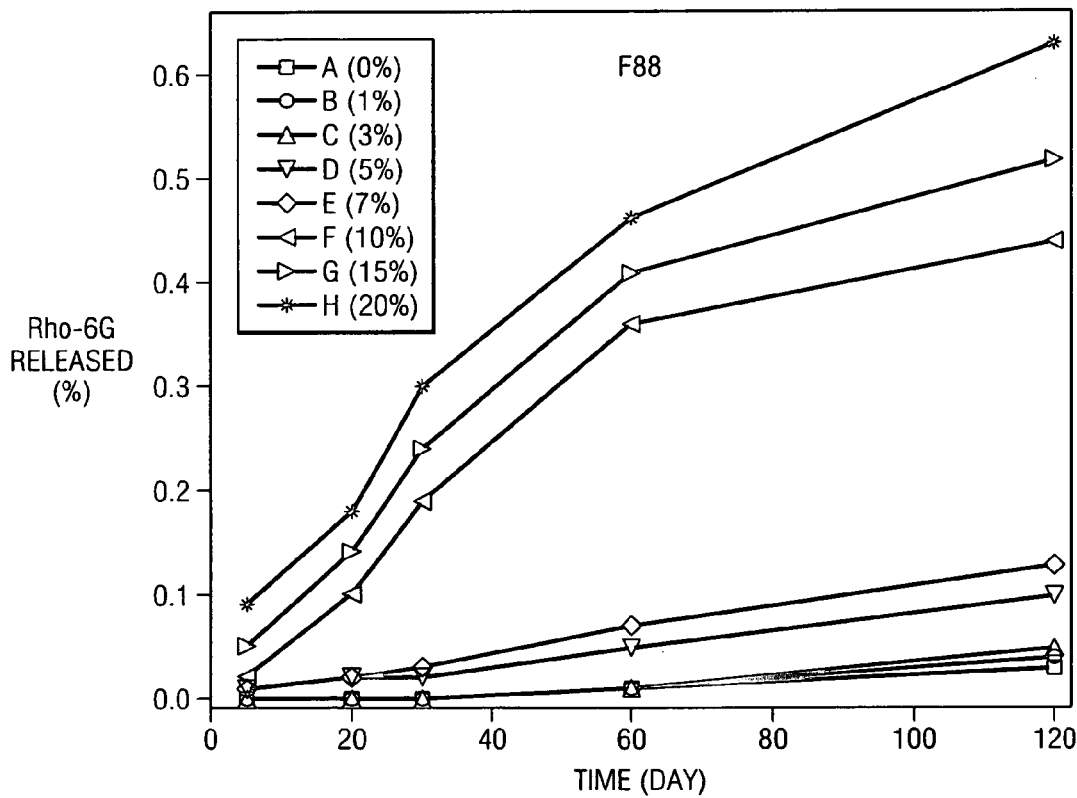
FIG. 5C is a graphical representation similar to FIGS. 5A and 5B showing the release profile of yet another block copolymer.

The percent release profiles of different block copolymers are shown in FIGS. 5A, 5B, and 5C. The overall release of L64 after a release duration of 130 days varied from 2% to 85%, and for P84, varied from 1% to 34%; for F88, varied from 3% to 63%. These results can be explained by the polymer elution process. L64 is smaller than P84 and F88 has larger hydrophilic section percentage (80%) over P84 (40%). Therefore, L64 and F88 elute faster than P84 and finally, will have better release characteristics.

The release profiles can be modified over a wide range through adjusting a number of factors, which means a release map can be established based on the combinatorial composition monolith libraries. A monolith with desired release characteristics can be easily located and then prepared according to this release map. The modified release characteristics include tuning the release rate, duration and dynamics. These characteristics are illustrated as follows: 1) the effect of block copolymer concentration on dye release as shown in FIGS. 3, 5A, 5B, and 5C; and 2) the effect of block copolymers on dye release as shown in FIGS. 4, 5A, 5B, and 5C. Ultimately, the release duration can be tuned with different polymers.

The controlled release function of the monolith is based on the forming of ordered silica/polymer architectures. It has previously been demonstrated that the evaporation-induced self-assembly (EISA) technique results in optically clear monoliths with an ordered mesophase. The mesostructured ordering of the dye-containing monoliths were characterized by low-angel X-ray diffraction (XRD) and transmission electron microscopy (TEM). As shown in FIG. 4, XRD peaks were observed at low angles, which are more and sharper with respect to the increasing polymer concentration. Using combination of the XRD data and TEM, structures of monoliths with different polymer concentration are clearly understood. For monoliths with 0%, 1% and 3% P84, that is, trace a, b and c (not shown in the XRD figure), with polymer concentrations below cmc, no peaks were observed in the XRD figure, which means there was limited formation of silica/polymer monodispersed structure in these monoliths. For monoliths with 5%, 7% and 10% P84, that is, trace d, e, and f, a broad peak was shown in the XRD pattern. The TEM images shown in FIGS. 5A, 5B, and 5C show typical worm-like structures. In this case the silica/polymer architectures were formed but limited long range order. In the XRD pattern of monoliths with 15% and 20% P84 (trace g and h), three peaks were observed that could be indexed as the (100), (110) and (200) reflections of a hexagonal mesostructure (p6 mm), which is also confirmed by TEM. With the increasing polymer concentration, the XRD peaks shifted to a lower angle, indicating a lager unit cell parameter. The XRD pattern and TEM image shown in FIGS. 5A, B, and C belong to the monolith after 2 months release. The preservation of the mesostructured ordering demonstrates that the polymer/silica matrix of the composite monolith remains stable after release of incorporated dyes.

The method of preparing mesostructured silica/block copolymer monoliths for use as a controlled release device and the resulting material having a release agent incorporated therein are useful in many fields. For use in the medical field of pharmaceuticals, the release agent may be applied in the form of small molecules, macromolecules (such as insulin), in drugs for ingestion or injection, drugs which are implanted, valve coating, stent coatings, and other related medical applications. The monoliths prepared according to the present invention are also applicable as biocidal coatings including anti-bacterial/antiviral coatings; mold inhibition, for example incorporating into paint and thereafter applying to building interiors; anti-biowarfare coatings; marine antifouling paints; woods preservatives; insecticidal coatings; and the like. Additionally, the monoliths prepared according to the present invention are useful for corrosion control. For example, coatings having polyvalent ions therein will employ the release agent to slowly release the polyvalent ions such as Cr, V, and Ce when exposed to environmental conditions conducive to corrosion of metals on which they are applied.

Although preferred embodiments of the invention have been illustrated in the accompanying Drawings and described in the foregoing Detailed Description, it will be understood that the invention is not limited to the embodiments disclosed, but is capable of numerous rearrangements, modifications, and substitutions of parts and elements without departing from the spirit of the invention.

The invention claimed is:

1. A method for forming a controlled release inorganic metal oxide material comprising the steps of:
   providing at least one release agent;
   providing a liquid source of an inorganic metal oxide;
   providing an amphiphilic block copolymer;
   providing a quantity of water;
   providing a catalyst;
   providing a co-solvent;
   preparing a solution comprising the liquid source of the inorganic metal oxide, the amphiphilic block copolymer, the water, the catalyst, and the co-solvent,
   dissolving the provided release agent into the prepared solution;
   heating the resulting solution at a controlled temperature;
   drying the resulting solution into a predetermined form;
   the resulting form having a release rate determined by the pore size of the inorganic metal oxide and the molecular weight of the amphiphilic block copolymer, wherein the inorganic metal oxide is silicia.

2. The method according to claim 1 wherein the silica comprises tetraethyl orthosilicate.

3. The method according to claim 1 wherein the silica comprises tetraethyl orthosilicate and an alkyl substituted silicate ester.

4. The method according to claim 3 wherein the alkyl substituted silicate ester comprises methyltriethoxysilane.

5. The method according to claim 1 wherein the defined pore size of the inorganic metal oxide is about 1 nm in diameter.

6. The method according to claim 1 wherein the defined pore size of the inorganic metal oxide is between about 1 nm and about 30 nm in diameter.

7. The method according to claim 1 wherein the defined pore size of the inorganic metal oxide is about 30 nm in diameter.

* * * * *